United States Patent
Hirt

(10) Patent No.: US 8,047,503 B2
(45) Date of Patent: Nov. 1, 2011

(54) CONICAL SPRING BUSHING

(75) Inventor: William J. Hirt, Oakland Township, MI (US)

(73) Assignee: Eaton Corporation, Cleveland, OH (US)

( * ) Notice: Subject to any disclaimer, the term of this patent is extended or adjusted under 35 U.S.C. 154(b) by 702 days.

(21) Appl. No.: 12/037,145

(22) Filed: Feb. 26, 2008

(65) Prior Publication Data

US 2009/0212245 A1     Aug. 27, 2009

(51) Int. Cl.
F16F 1/00     (2006.01)

(52) U.S. Cl. .......................... 251/64; 251/337

(58) Field of Classification Search ............. 251/64, 251/129.15, 337; 267/161
See application file for complete search history.

(56) References Cited

U.S. PATENT DOCUMENTS

| | | | | |
|---|---|---|---|---|
| 2,179,469 A * | 11/1939 | Germonpres | ............. | 267/141.7 |
| 2,706,491 A * | 4/1955 | Kohler | ............. | 137/540 |
| 2,881,980 A * | 4/1959 | Goodrich et al. | ............. | 239/562 |
| 3,007,720 A * | 11/1961 | Breitenstein | ............. | 285/268 |
| 4,084,843 A * | 4/1978 | Gassert | ............. | 285/105 |
| 4,285,054 A * | 8/1981 | McNeel | ............. | 367/183 |
| 4,336,823 A * | 6/1982 | Staiger et al. | ............. | 137/270 |
| 4,465,267 A * | 8/1984 | Chatelin | ............. | 267/161 |
| 4,480,490 A * | 11/1984 | Inoue | ............. | 74/401 |
| 4,502,256 A * | 3/1985 | Hahn | ............. | 52/63 |
| 4,569,504 A * | 2/1986 | Doyle | ............. | 251/129.15 |
| 4,635,683 A * | 1/1987 | Nielsen | ............. | 137/625.65 |
| 4,773,445 A * | 9/1988 | Visket | ............. | 137/595 |
| 4,795,098 A | 1/1989 | Kirchner et al. | | |
| 4,976,405 A | 12/1990 | Graner et al. | | |
| 5,915,677 A * | 6/1999 | Yajima et al. | ............. | 267/161 |
| 5,924,492 A * | 7/1999 | Kikuchi et al. | ............. | 169/37 |
| 6,079,435 A * | 6/2000 | Franz et al. | ............. | 137/82 |
| 6,386,220 B1 * | 5/2002 | Koenings | ............. | 137/15.21 |
| 6,547,214 B2 * | 4/2003 | Gregoire | ............. | 251/58 |
| 6,668,849 B2 * | 12/2003 | Onstenk et al. | ............. | 137/1 |
| 6,698,399 B1 | 3/2004 | Grabert | | |
| 6,799,734 B1 | 10/2004 | Hans | | |
| 6,918,571 B1 | 7/2005 | Rose | | |
| 7,159,843 B1 * | 1/2007 | Mullally et al. | ............. | 251/129.16 |
| 2005/0001366 A1 | 1/2005 | Hederstierna | | |

* cited by examiner

Primary Examiner — John Bastianelli
(74) Attorney, Agent, or Firm — Dykema Gossett PLLC

(57) ABSTRACT

A bushing for positioning between a first component and a second component is disclosed. The bushing comprises a conical body that includes a first edge, a second edge, and at least one slot extending from the first edge toward the second edge. The slot or slots facilitate the flexing of the conical body. Methods for making a conical bushing are also disclosed.

15 Claims, 2 Drawing Sheets

CONICAL SPRING BUSHING

TECHNICAL FIELD

The present invention relates to bushings, including bushings for use in valves.

BACKGROUND

Valves may be employed for controlling flow of pressurized hydraulic fluid to actuators in hydraulic systems. Some valves may be solenoid operated (e.g., operated in response to an electrical control signal). In a traditional solenoid operated valve, a spring and bearing may be disposed within a magnetic flux collector. An operating member (e.g., a rod or a pin) may be slidably disposed in the bearing, and the operating member may have an armature received thereover. Although in some designs, a flat flapper bearing or spider bearing may be disposed around the operating member; they do not typically allow great displacement. In some valves, an undesired phenomenon referred to as "magnetic side loading and latching" may occur in which the armature comes close to contact with the magnetic flux collector due to the needed tolerance and the resultant excessive clearance between the operating member and the bearing. When this magnetic side loading or latching occurs, the armature may move from side to side within the flux collector, as opposed to strictly up and down within the flux collector, which may impair operation of the valve.

SUMMARY

A bushing for positioning between a first component and a second component is disclosed. The bushing comprises a conical body that includes a first edge, a second edge, and at least one slot extending from the first edge toward the second edge. The slot or slots facilitate the flexing of the conical body. Methods for making a conical bushing are also disclosed.

BRIEF DESCRIPTION OF THE DRAWINGS

Embodiments of the invention will now be described, by way of example, with reference to the accompanying drawings, wherein.

DETAILED DESCRIPTION

Reference will now be made in detail to embodiments of the present invention, examples of which are described herein and illustrated in the accompanying drawings. While the invention will be described in conjunction with embodiments, it will be understood that they are not intended to limit the invention to these embodiments. On the contrary, the invention is intended to cover alternatives, modifications and equivalents, which may be included within the spirit and scope of the invention as embodied by the appended claims.

Figure 1:
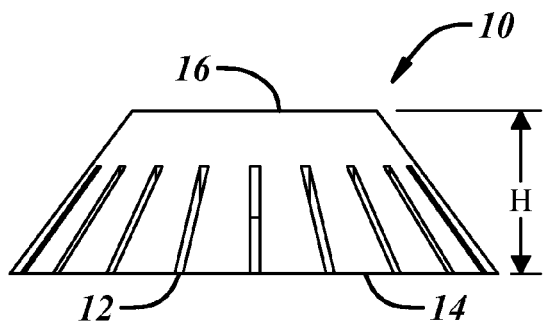
FIG. 1 is a side view of a bushing according to an embodiment of the invention.
Figure 3:
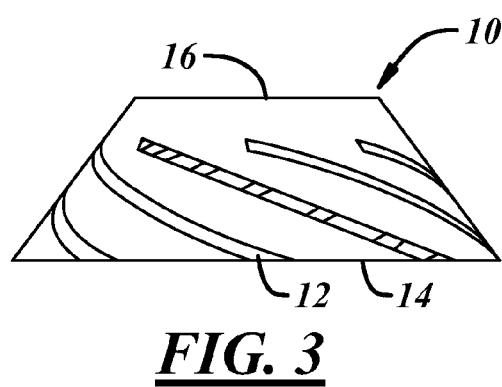
FIG. 3 is a side view of a bushing according to an embodiment of the invention.

A side view of a bushing 10 according to embodiments of the invention are generally shown in FIG. 1 and FIG. 3. Bushing 10 may comprise a formed "cone" or "conical" configuration, which may take the form of various cone-like or truncated cone configurations including, without limitation, the configurations generally illustrated in the drawing figures. Bushing 10 may be configured to facilitate a spring effect or action with respect to connected components. The height of the formed cone—designated H in FIG. 1 for purposes of general reference—may change through the course of the bushing's application or use. That is, the height H of bushing 10 may decrease as the bushing is compressed and may increase as the bushing expands.

In an embodiment, bushing 10 may be formed from a work piece, which may be flat or substantially flat. Moreover, for a number of applications, the work piece may be relatively thin. For example, without limitation, the work piece may be approximately 0.10 mm inches to approximately 0.25 mm in thickness. Moreover, the work piece may be, but is not required to be, of uniform or substantially uniform thickness. The work piece may be substantially round in an embodiment.

In an embodiment, the work piece may comprise precipitation hardened 17-4 stainless steel. Although this material is mentioned in detail, it is understood by those of ordinary skill in the art that the work piece may comprise other types of materials and remain within the spirit and scope of the invention. For example, in other embodiments, the work piece may comprise 17-7 stainless steel, other types of stainless steel, other metals, other plastics, or numerous other types of materials, provided the formed bushing can adequately to meet necessary or desired functional and operational requirements.

The work piece may be formed (e.g., stamped) with at least one relief slot 12. Relief slot 12 may be stamped or may be photochemically created (e.g., chemically etched). Relief slot 12 may be provided to facilitate flexing (e.g., a height H reduction and/or expansion) of bushing 10. In an embodiment, bushing 10 includes a plurality of slots 12. The work piece may be formed to include one or more relief slots 12, and then may be further formed into a generally cone-like or conical shape. Alternatively, one or more relief slots 12 may be formed in the work piece after it has been formed into a generally cone-like or conical shaped bushing. Once the bushing is generally formed, as viewed in side elevation, the bushing may include a first edge 14 and a second opposing edge 16.

Figure 2:
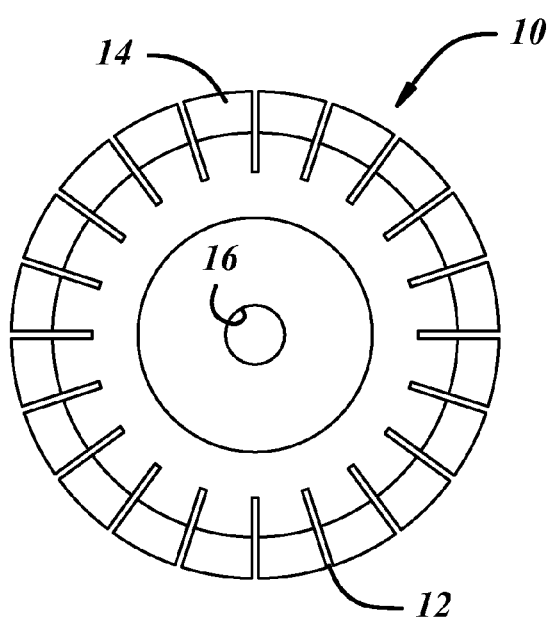
FIG. 2 is top plan view of a bushing according to an embodiment of the invention.

In an embodiment, bushing 10 may include a plurality of relief slots 12, which can be configured to be uniformly spaced around first edge 14 of bushing 10. As generally illustrated in the embodiment shown in FIGS. 1 and 2, one or more slots 12 may extend radially inwardly from first edge 14 of bushing 10. Such one or more slots 12 may extend from first edge 14 to a point located between first edge 14 and second edge 16. Moreover, in an embodiment, a plurality of slots 12 extend at least half the distance (e.g., radial distance) between first edge 14 and second edge 16.

Figure 4:
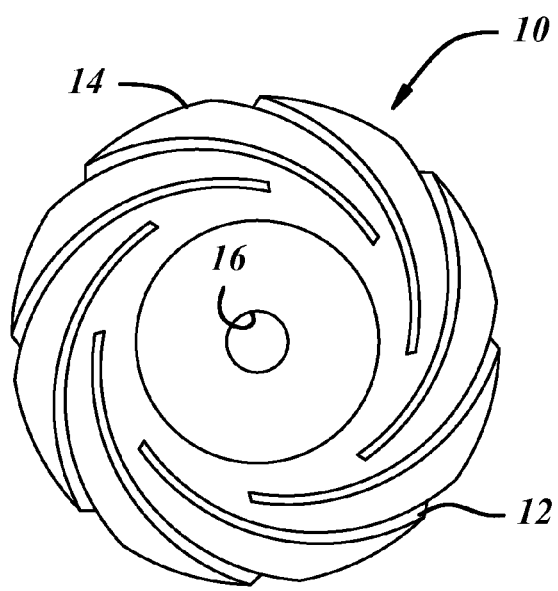
FIG. 4 is a top plan view of a bushing according to an embodiment of the invention.

As generally illustrated in the embodiments illustrated in FIGS. 3 and 4, slots 12 may extend inwardly from first edge 14 of bushing 10 in a non-linear manner, or at an angle. Moreover, as illustrated in FIGS. 3 and 4, one or more slots 12 may curve (viewed from a side elevation and/or from a top plan perspective) to some degree as slot 12 extends inwardly from first edge 14. Slots 12 may curve to form an angle that ranges between extending circumferentially around edge 14 of bushing 12 to extending directly radially inwardly from first edge 14."

The width of one or more slots 12 may affect and/or control the amount of flexing associated with a bushing 12. For example, all other things being generally equivalent, wider slots 12 will typically permit a greater amount of flexing of bushing 12 as compared to an equal number of comparatively thinner slots 12. Accordingly, wider slots may provide a comparatively lower spring action or spring effect than thinner slots in an otherwise similar bushing. Furthermore, the configuration of slots 12 may also affect the amount of flexing of bushing 12. For example, slots that extend inwardly at an angle may allow for a greater amount of flexing of bushing 12 than slots that extend radially inwardly (e.g., slots that are more perpendicular to edge 14 of bushing 12). Accordingly, curved or angled slots may provide a lower spring action or spring effect than slots that are comparatively more perpendicular.

Bushing 10 may be provided between two surfaces and may provide a flexing action or effect between the surfaces during displacement. The length or range of displacement may determine the effectiveness of avoidance to permanent deflection. The conical bushing may provide for greater displacement than a flat flapper bearing or spider bearing.

Figure 5:
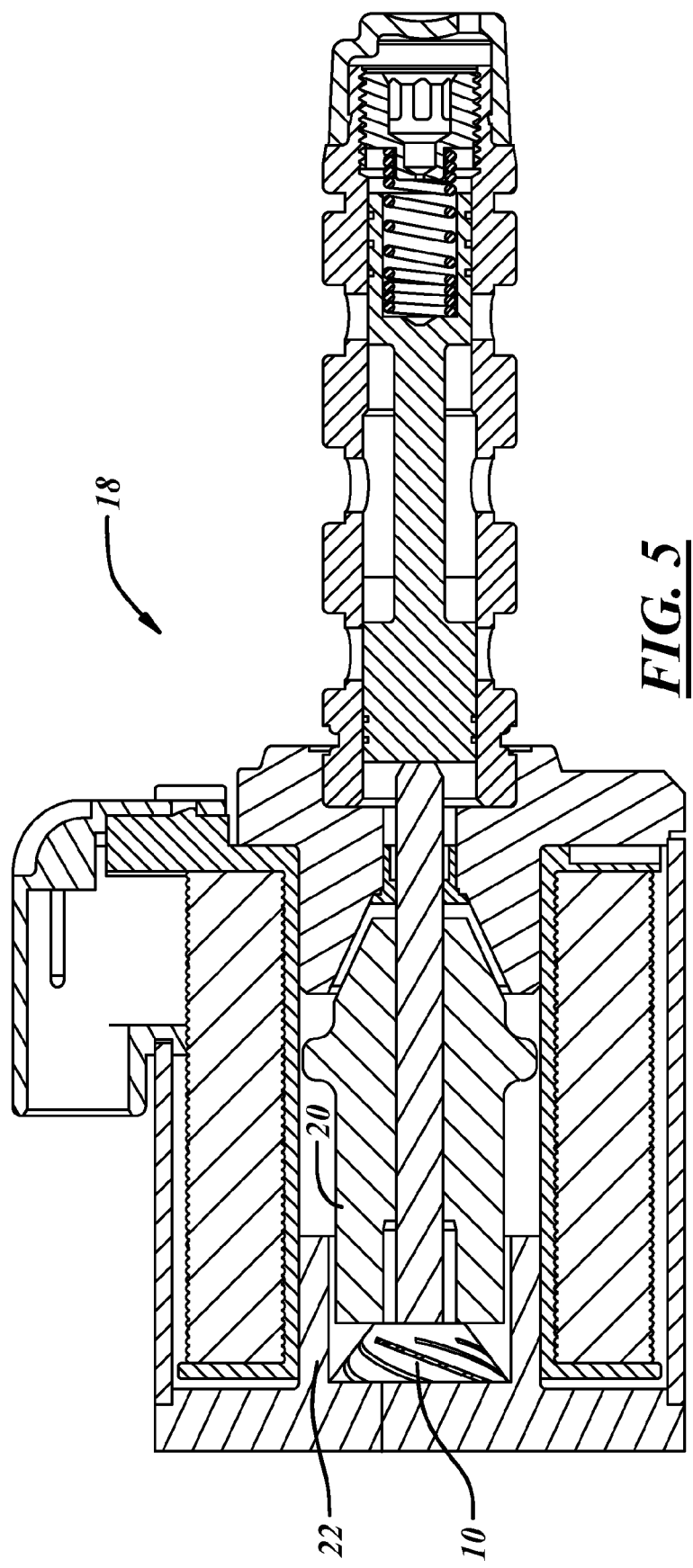
FIG. 5 is a cross-sectional view of a valve including a bushing according to an embodiment of the invention.

Referring to FIG. 5, an embodiment of a bushing is illustrated in connection with a valve 18. By way of example, without limitation, valve 18 may comprise a solenoid-operated valve 18, and may include a bushing 10 that is provided between an armature 20 and a magnetic flux collector 22. A first end of bushing 10 (i.e., the end comprising edge 14) may be approximately equal in width (or diameter) to a recess or receiving portion located in or associated with magnetic flux collector 22. In an embodiment, the first end of bushing 10 may be approximately 12 mm. A second end of bushing 10 (i.e., the end comprising edge 16) may be comparatively smaller in width (or diameter) than the first end (i.e., the end closer in proximity to the magnetic flux collector 22). In an embodiment, the second end of bushing 10 may be approximately 6 mm. Although the foregoing dimensions associated with the bushing 10 are mentioned in detail, it is understood by those of ordinary skill in the art that various other dimensions may be utilized for bushing 10 and remain within the spirit and scope of the invention.

Embodiments of the invention may involve a valve configuration in which a bushing 10 is provided between two components that may be controllably drawn together. For example, as generally illustrated in FIG. 5, a bushing 10 may be provided between an armature 20 and a flux collector 22. In operation, armature 20 may be attracted to magnetic flux collector 22, for example, if activated by an electrical control signal. As armature 20 is attracted or otherwise moves toward magnetic flux collector 22, the force exerted upon bushing 10 may eventually cause bushing 10 to compress or flex. When the attraction or force applied to the armature 20 toward the flux collector 22 is ended or sufficiently lessened, for example when an associated control signal is reduced or ceased, the decompression or expansion force associated with the bushing 10 may provide a force against armature 20, which may help to maintain armature 20 away from magnetic flux collector 22.

The generally conical shape of bushing 10, which may take the form of a truncated cone (viewed in cross section) may permit a first end 14 of bushing 10 to engage magnetic flux collector 22 and the second end 16 to move more freely within valve 18. That is, such a configuration can permit an exterior surface of bushing 10 to move within an interior cavity of the valve 18 with a lessened potential for surfaces of bushing 10 to rub against portions or components of valve 18. The shape of bushing 10 may also limit excess clearance between the operating member and bearing of a valve and may prevent armature 20 from coming into contact with magnetic flux collector 22, thereby hindering "magnetic latching."

The inventive concept includes a method for making a bushing that is suitable for use in a valve assembly. The method comprises forming a work piece and forming the work piece into a conical bushing, including those of the types previously described. In an embodiment, a work piece—which may be flat or substantially flat—is formed to a desired configuration. In an embodiment, the work piece will be formed substantially in the shape of a circle. A substantially circular opening may be formed in approximately the center of the work piece. In a first embodiment, at least one slot is formed in the work piece before the work piece is formed into a generally conical configuration. The slot may extend inwardly from an outer edge of the work piece. The slot may extend directly radially inwardly from the outer edge of the work piece or may curve to form an angle that ranges between extending circumferentially around the outer edge of the work piece to extending directly radially inwardly from the outer edge of the work piece. The slot may be stamped or photochemically created (e.g., chemically etched). In an alternate embodiment, one or more slots are formed during or after the work piece is formed into a generally conical configuration.

The formed work piece may then be formed into a conical configuration. For example, the work piece may be stamped to its desired conical shape using a progressive stamping die. The work piece may then undergo a heat treatment process (e.g., similar to the heat treatment process conventionally used for springs to improve the uniformity and strength of the formed work piece). The heat treatment process may help ensure that the formed work piece retains its shape and spring rate. In an embodiment, the conically-shaped work piece may undergo heat treatment without being held in any tooling. In another embodiment, the conically-shaped work piece may be held in tooling during the heat treatment process to help the work piece maintain its conical shape. Tooling may be used when tighter tolerances are desired, for example.

The formed work piece may then be placed or otherwise provided in a valve between a first component (e.g., an armature) and a second component (e.g., a flux collector) that may move to and from one another.

The foregoing descriptions of specific embodiments of the present invention have been presented for purposes of illustration and description. They are not intended to be exhaustive or to limit the invention to the precise forms disclosed, and various modifications and variations are possible in light of the above teaching. The embodiments were chosen and described in order to explain the principles of the invention and its practical application, to thereby enable others skilled in the art to utilize the invention and various embodiments with various modifications as are suited to the particular use contemplated. It is intended that the scope of the invention be defined by the claims appended hereto and their equivalents.

What is claimed is:

1. A bushing for positioning between a first component and a second component, the bushing comprising:
a one-piece, substantially planar workpiece formed into a conical body including:
a first edge at a first axial end of the conical body,
a second edge at a second axial end of the conical body, and
a plurality of slots originating from and circumferentially spaced around the first edge of the conical body and extending from the first edge toward the second edge, wherein each of the plurality of slots extends radially inwardly, wherein each of the plurality of slots has a constant width, wherein each of the plurality of slots defines an angle between each of the plurality of slots and the first edge that is more than 0 degrees and that is less than 90 degrees; and wherein at least one of the plurality of slots facilitates the flexing of the conical body.

2. A bushing in accordance with claim 1, wherein the slots are substantially uniformly spaced around the first edge of the body.

3. A bushing in accordance with claim 1, wherein the plurality of slots extend radially inwardly from the first edge of the body.

4. A bushing in accordance with claim 1, wherein each of the plurality of slots extend from the first edge of the body to a point located between the first edge of the body and the second edge of the body.

5. A bushing in accordance with claim 1, wherein the width of at least one of the plurality of slots or the configuration of at least one of the plurality of slots are configured to provide an amount or range of flexing of the bushing.

6. A bushing in accordance with claim 1, wherein the body has a thickness that is between about 0.10 mm and about 0.25 mm.

7. A bushing in accordance with claim 1, wherein the bushing is configured for disposal in a valve assembly between a first component and a second component, wherein the first component is controllably forced or attracted toward the second component.

8. A bushing in accordance with claim 7, wherein the first component comprises an armature and the second component comprises a magnetic flux collector.

9. A bushing in accordance with claim 7, wherein the first edge of the bushing is approximately equal in diameter or width to a recess located in the second component.

10. A bushing in accordance with claim 7, wherein the second edge of the bushing is smaller in diameter or width than a recess located in the second component.

11. A bushing in accordance with claim 1, wherein the body comprises metal.

12. A bushing in accordance with claim 1, wherein the body comprises stainless steel.

13. A bushing in accordance with claim 1, wherein the body comprises plastic.

14. A valve assembly comprising:

an armature;

a member opposing the armature; and a bushing disposed between the armature and the member opposing the armature, the bushing comprising a conical body and including a first edge, a second edge, and at least one slot extending from the first edge toward the second edge, wherein the at least one slot extends radially inwardly, wherein the at least one slot has a constant width, wherein the at least one slot defines an angle between the at least one slot and the first edge that is more than 0 degrees and that is less than 90 degrees; and wherein the at least one slot is configured to facilitate flexing or compression of the body in response to a force exerted on the bushing when the armature contacts the bushing and moves toward the member opposing the armature.

15. A bushing in accordance with claim 1, wherein at least one of the plurality of slots is disposed at an angle that ranges between the at least one of the plurality of slots extending circumferentially around the first edge of the bushing to the at least one of the plurality of slots extending directly radially inwardly from the first edge.

* * * * *